(12) United States Patent
Veronesi

(10) Patent No.: US 11,974,881 B2
(45) Date of Patent: May 7, 2024

(54) METHOD AND SYSTEM FOR PROVIDING AN ANATOMIC ORIENTATION INDICATOR WITH A PATIENT-SPECIFIC MODEL OF AN ANATOMICAL STRUCTURE OF INTEREST EXTRACTED FROM A THREE-DIMENSIONAL ULTRASOUND VOLUME

(71) Applicant: GE Precision Healthcare LLC, Wauwatosa, WI (US)

(72) Inventor: Federico Veronesi, Bologna (IT)

(73) Assignee: GE Precision Healthcare LLC, Waukesha, WI (US)

( * ) Notice: Subject to any disclaimer, the term of this patent is extended or adjusted under 35 U.S.C. 154(b) by 0 days.

(21) Appl. No.: 17/003,247

(22) Filed: Aug. 26, 2020

(65) Prior Publication Data

US 2022/0061809 A1    Mar. 3, 2022

(51) Int. Cl.
*A61B 8/00*    (2006.01)
*A61B 8/08*    (2006.01)
(Continued)

(52) U.S. Cl.
CPC .............. *A61B 8/463* (2013.01); *A61B 8/466* (2013.01); *A61B 8/469* (2013.01); *A61B 8/483* (2013.01); *A61B 8/5207* (2013.01); *G06T 17/00* (2013.01); *G06T 19/00* (2013.01); *G16H 30/40* (2018.01); *G16H 50/50* (2018.01); *G06N 3/04* (2013.01); *G06N 3/08* (2013.01); *G06T 2210/41* (2013.01); *G16H 50/20* (2018.01)

(58) Field of Classification Search
CPC ......... A61B 8/463; A61B 8/466; A61B 8/469; A61B 8/483; A61B 8/5207; G06T 17/00; G06T 19/00; G06T 2210/41; G16H 30/40; G16H 50/50
See application file for complete search history.

(56) References Cited

U.S. PATENT DOCUMENTS 9,211,105 B2 * 12/2015 Hyun ................... A61B 8/4254
2008/0238916 A1 * 10/2008 Ghosh ...................... G06T 19/00
345/419

(Continued)

*Primary Examiner* — Colin T. Sakamoto
*Assistant Examiner* — Andrew W Begeman
(74) *Attorney, Agent, or Firm* — McAndrews, Held & Malloy, Ltd.; Daniel Bissing; David Bates

(57) ABSTRACT

A system and method for providing an anatomic orientation indicator with a patient-specific model of an anatomical structure of interest extracted from a three-dimensional (3D) ultrasound volume is provided. The method includes extracting the anatomical structure of interest from the 3D volume and generating a patient-specific model of the anatomical structure of interest. The method includes generating an anatomic orientation indicator including at least one mocked patient anatomy model of an anatomical structure adjacent the anatomical structure of interest at a position and orientation relative the patient-specific model. The method includes displaying the anatomic orientation indicator with the patient-specific model at a same first point of view. The method includes receiving an instruction to change a point of view of the patient-specific model to a second point of view and updating the displaying of the anatomic orientation indicator with the patient-specific model to the second point of view.

20 Claims, 6 Drawing Sheets

(51) Int. Cl.
*G06T 17/00* (2006.01)
*G06T 19/00* (2011.01)
*G16H 30/40* (2018.01)
*G16H 50/50* (2018.01)
G06N 3/04 (2023.01)
G06N 3/08 (2023.01)
G16H 50/20 (2018.01)

(56) References Cited

U.S. PATENT DOCUMENTS

| | | | |
|---|---|---|---|
| 2009/0177454 A1* | 7/2009 | Bronstein | G06T 17/20 |
| | | | 703/11 |
| 2014/0148677 A1* | 5/2014 | Liempde | A61B 5/065 |
| | | | 600/389 |
| 2018/0085203 A1* | 3/2018 | Ramirez | G06F 30/00 |
| 2018/0296167 A1* | 10/2018 | Stewart | A61B 5/339 |
| 2019/0200964 A1* | 7/2019 | Sudhakar | A61B 8/4254 |
| 2020/0405264 A1* | 12/2020 | Labyed | G01S 7/52073 |

* cited by examiner

METHOD AND SYSTEM FOR PROVIDING AN ANATOMIC ORIENTATION INDICATOR WITH A PATIENT-SPECIFIC MODEL OF AN ANATOMICAL STRUCTURE OF INTEREST EXTRACTED FROM A THREE-DIMENSIONAL ULTRASOUND VOLUME

FIELD

Certain embodiments relate to ultrasound imaging. More specifically, certain embodiments relate to a method and system for providing an anatomic orientation indicator with a patient-specific model of an anatomical structure of interest extracted from a three-dimensional (3D) ultrasound volume. The anatomic orientation indicator may comprise one or more mocked patient anatomy models of nearby anatomical structures. The anatomic orientation indicator may provide a same point of view as the patient-specific model to present spatial contextual information to a viewer of the patient-specific model. The point of view of the anatomic orientation indicator may be updated to match a point of view of the patient-specific model as the point of view of the patient-specific model is changed.

BACKGROUND

Ultrasound imaging is a medical imaging technique for imaging organs and soft tissues in a human body. Ultrasound imaging uses real time, non-invasive high frequency sound waves to produce two-dimensional (2D), three-dimensional (3D), and/or four-dimensional (4D) (i.e., real-time/continuous 3D images) images.

Ultrasound imaging is a valuable, non-invasive tool for diagnosing various medical conditions. For example, ultrasound image volumes may be used to generate a patient-specific 3D model of an anatomical structure of interest that may be viewed to identify anatomical anomalies. However, users may have difficulty understanding an orientation of the patient-specific 3D model with respect to nearby patient anatomy when viewing the patient-specific 3D model. For example, if a user is viewing a patient-specific 3D model of a tricuspid valve, the user may have difficulty determining the positions and/or orientations of nearby anatomical structures, such as an aortic valve and/or a mitral valve. Moreover, the difficulty in recognizing a spatial context of the presented patient-specific 3D model with respect to nearby anatomical structures may increase as a user interactively changes the point of view of the patient-specific 3D model.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for providing an anatomic orientation indicator with a patient-specific model of an anatomical structure of interest extracted from a three-dimensional (3D) ultrasound volume, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Figure 1:
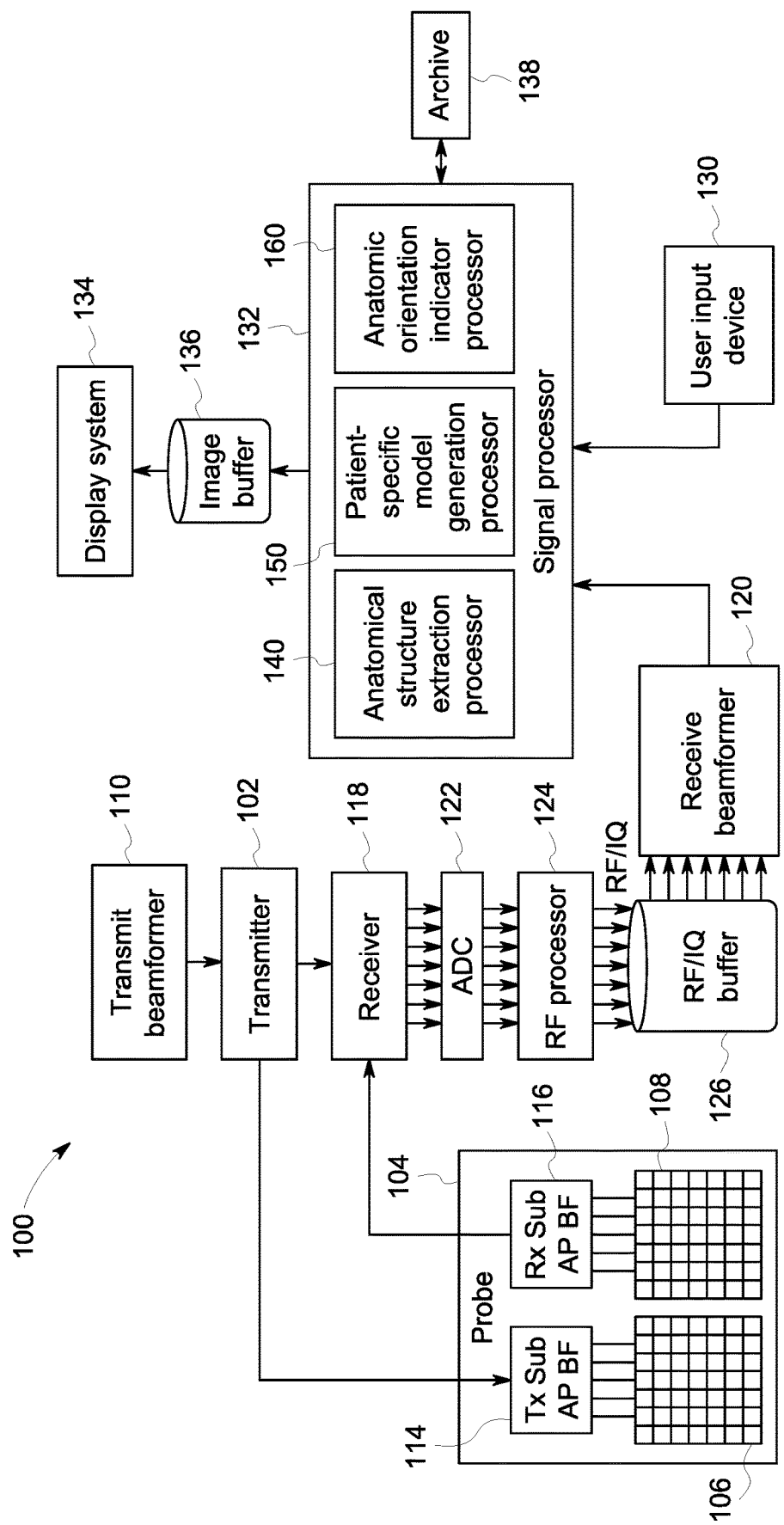
FIG. 1 is a block diagram of an exemplary ultrasound system that is operable to provide an anatomic orientation indicator with a patient-specific model of an anatomical structure of interest extracted from a three-dimensional (3D) ultrasound volume, in accordance with various embodiments.

Certain embodiments may be found in a method and system for providing an anatomic orientation indicator with a patient-specific model of an anatomical structure of interest extracted from a three-dimensional (3D) ultrasound volume. Various embodiments have the technical effect of providing visualization of a spatial context for a patient-specific model presented at a display system by presenting an anatomic orientation indicator comprising one or more mocked patient anatomy models of nearby (e.g., adjacent, surrounding, and/or immediate vicinity) anatomical structures at a same point of view as the patient-specific model. Aspects of the present disclosure have the technical effect of updating the point of view of the anatomic orientation indicator to match a point of view of the patient-specific model as the point of view of the patient-specific model is changed.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general-purpose signal processor or a block of random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mode, PW Doppler, CW Doppler, MGD, and/or sub-modes of B-mode and/or CF such as Shear Wave Elasticity Imaging (SWEI), TVI, Angio, B-flow, BMI, BMI_Angio, and in some cases also MM, CM, TVD where the "image" and/or "plane" includes a single beam or multiple beams.

Furthermore, the term processor or processing unit, as used herein, refers to any type of processing unit that can carry out the required calculations needed for the various embodiments, such as single or multi-core: CPU, Accelerated Processing Unit (APU), Graphics Board, DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

FIG. 1 is a block diagram of an exemplary ultrasound system 100 that is operable to provide an anatomic orientation indicator 220, 320, 420, 520 with a patient-specific model 210, 310, 410, 422, 510 of an anatomical structure of interest extracted from a three-dimensional (3D) ultrasound volume, in accordance with various embodiments. Referring to FIG. 1, there is shown an ultrasound system 100. The ultrasound system 100 comprises a transmitter 102, an ultrasound probe 104, a transmit beamformer 110, a receiver 118, a receive beamformer 120, A/D converters 122, a RF processor 124, a RF/IQ buffer 126, a user input device 130, a signal processor 132, an image buffer 136, a display system 134, and an archive 138.

The transmitter 102 may comprise suitable logic, circuitry, interfaces and/or code that may be operable to drive an ultrasound probe 104. The ultrasound probe 104 may comprise a two dimensional (2D) array of piezoelectric elements. The ultrasound probe 104 may comprise a group of transmit transducer elements 106 and a group of receive transducer elements 108, that normally constitute the same elements. In certain embodiment, the ultrasound probe 104 may be operable to acquire ultrasound image data covering at least a substantial portion of an anatomy, such as the heart, a blood vessel, or any suitable anatomical structure.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive the signals from the receive sub-aperture beamformer 116. The analog signals may be communicated to one or more of the plurality of A/D converters 122.

The plurality of A/D converters 122 may comprise suitable logic, circuitry, interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The receive beamformer 120 may comprise suitable logic, circuitry, interfaces and/or code that may be operable to perform digital beamforming processing to, for example, sum the delayed channel signals received from RF processor 124 via the RF/IQ buffer 126 and output a beam summed signal. The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital. In various embodiments, the ultrasound system 100 comprises a plurality of receive beamformers 120.

The user input device 130 may be utilized to input patient data, scan parameters, settings, select protocols and/or templates, select landmarks 212, 312, 412, 512 of an anatomical structure in a 3D volume, manipulate a point of view of a patient-specific model, and the like. In an exemplary embodiment, the user input device 130 may be operable to configure, manage and/or control operation of one or more components and/or modules in the ultrasound system 100. In this regard, the user input device 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input device 130, the signal processor 132, the image buffer 136, the display system 134, and/or the archive 138. The user input device 130 may include button(s), rotary encoder(s), a touchscreen, a touch pad, a trackball, motion tracking, voice recognition, a mousing device, keyboard, camera and/or any other device capable of receiving a user directive. In certain embodiments, one or more of the user input devices 130 may be integrated into other components, such as the display system 134, for example. As an example, user input device 130 may include a touchscreen display.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), an enterprise archive (EA), a vendor-neutral archive (VNA), or any suitable device for storing images and related information.

The signal processor 132 may be one or more central processing units, microprocessors, microcontrollers, and/or the like. The signal processor 132 may be an integrated component, or may be distributed across various locations, for example. In an exemplary embodiment, the signal processor 132 may comprise an anatomical structure extraction processor 140, a patient-specific model generation processor 150, and an anatomic orientation indicator processor 160. The signal processor 132 may be capable of receiving input information from a user input device 130 and/or archive 138, receiving image data, generating an output displayable by a display system 134, and manipulating the output in response to input information from a user input device 130, among other things. The signal processor 132, including the anatomical structure extraction processor 140, the patient-specific model generation processor 150, and the anatomic orientation indicator processor 160, may be capable of executing any of the method(s) and/or set(s) of instructions discussed herein in accordance with the various embodiments, for example.

The ultrasound system 100 may be operable to continuously acquire ultrasound scan data at a frame rate that is suitable for the imaging situation in question. Typical frame rates range from 20-120 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes' worth of frames of ultrasound scan data. The frames of ultrasound scan data are stored in a manner to facilitate retrieval thereof according to its order or time of acquisition. The image buffer 136 may be embodied as any known data storage medium.

The signal processor 132 may include an anatomical structure extraction processor 140 that comprises suitable logic, circuitry, interfaces and/or code that may be operable to extract an anatomical structure of interest from a 3D volume. For example, the anatomical structure extraction processor 140 may be used to extract a valve, ventricle, or vessel of a heart. The anatomical structure extraction processor 140 may extract the anatomical structure of interest from the 3D volume using image segmentation, manual tracing, and/or any suitable anatomical structure extraction technique. For example, the anatomical structure extraction processor 140 may receive a manual tracing of boundaries of the anatomical structure of interest in the image data via the user input device 130. The manual tracing may be used by the anatomical structure extraction processor 140 to extract anatomical structure of interest information from the 3D volume. An another example, the anatomical structure extraction processor 140 may receive identifications of landmarks 212, 312, 412, 512 of the anatomical structure of interest via the user input device 130 that may be used by the anatomical structure extraction processor 140 to segment the anatomical structure of interest in the 3D volume. For example, a user that desires to extract a tricuspid valve from a 3D volume may select a tricuspid valve tool to select landmarks 212, 312, 412, 512 of a tricuspid valve depicted in the image data. The landmarks 212, 312, 412, 512 may be used by the anatomical structure extraction processor 140 to segment the tricuspid valve in the 3D volume.

Additionally and/or alternatively, the anatomical structure extraction processor 140 may include, for example, artificial intelligence image analysis algorithms, one or more deep neural networks (e.g., a convolutional neural network such as u-net) and/or may utilize any suitable form of artificial intelligence image analysis techniques or machine learning processing functionality configured to provide segmentation functionality. The artificial intelligence image analysis techniques or machine learning processing functionality configured to provide the segmentation may additionally and/or alternatively be provided by a different processor or distributed across multiple processors at the ultrasound system 100 and/or a remote processor communicatively coupled to the ultrasound system 100. For example, the image segmentation functionality may be provided as a deep neural network that may be made up of, for example, an input layer, an output layer, and one or more hidden layers in between the input and output layers. Each of the layers may be made up of a plurality of processing nodes that may be referred to as neurons. For example, the image segmentation functionality may include an input layer having a neuron for each pixel or a group of pixels from a 3D volume of an anatomical structure. The output layer may have a neuron corresponding to a plurality of pre-defined anatomical structures, such as a tricuspid valve, mitral valve, aortic valve, left ventricle, right ventricle, or any suitable anatomical structure. Each neuron of each layer may perform a processing function and pass the processed image information to one of a plurality of neurons of a downstream layer for further processing. As an example, neurons of a first layer may learn to recognize edges of structure in the image data. The neurons of a second layer may learn to recognize shapes based on the detected edges from the first layer. The neurons of a third layer may learn positions of the recognized shapes relative to landmarks in the image data. The processing performed by the deep neural network may identify anatomical structures and the location of the structures in the 3D volume with a high degree of probability.

In an exemplary embodiment, the anatomical structure extraction processor 140 may be configured to store the extracted anatomical structure information at archive 138 and/or any suitable storage medium. The extracted anatomical structure information may be provided to the patient-specific model generation processor 150.

The signal processor 132 may include a patient-specific model generation processor 150 that comprises suitable logic, circuitry, interfaces and/or code that may be operable to generate a patient-specific model based on the extracted anatomical structure of interest information. For example, the patient-specific model generation processor 150 may be configured to perform polygonal modeling, point cloud modeling, curve modeling, digital sculpting, and/or any suitable 3D modeling technique and/or algorithm using the extracted anatomical structure of interest information to generate a patient-specific model.

The signal processor 132 may include an anatomic orientation indicator processor 160 that comprises suitable logic, circuitry, interfaces and/or code that may be operable to generate and present an anatomic orientation indicator with the patient-specific model. The anatomic orientation indicator and patient-specific model may be presented at a same point of view to provide spatial context of the patient-specific model with respect to nearby anatomical structures. The anatomic orientation indicator may comprise one or more mocked patient anatomy models defined based on anatomical knowledge. For example, the mocked patient anatomy model(s) may be defined using average shape, dimensions, and orientation reported in scientific literature. The mocked patient anatomy models may be selected and retrieved from archive 138 or any suitable data storage medium based on an association with an anatomical structure of the patient-specific model.

As an example, mocked patient anatomy models of an aortic valve and a mitral valve may be retrieved from archive 138 or any suitable data storage medium by the anatomic orientation indicator processor 160 in response to the generation of a tricuspid valve patient-specific model. The mitral valve annulus mocked patient anatomy model, for example, may be defined based on scientifically reported data about shape (e.g., non-planar saddle-shaped and D-shaped on short-axis) and size (e.g., main axis average length, anterior point height with respect to valvular plane, and the like). The position of the mitral valve annulus mocked patient anatomy model may be defined based on scientific data with respect to the aortic valve annulus and/or tricuspid valve. For example, the positions and/or orientations of the mitral valve annulus mocked patient anatomy model and/or the aortic valve annulus mocked patient anatomy model may be defined by scientifically reported data that the aortic annulus is anterior to the mitral valve and the two annuli are skewed an average of 135 degrees apart.

The anatomic orientation indicator processor 160 may comprise suitable logic, circuitry, interfaces and/or code that may be operable to generate the anatomic orientation indicator comprising the mocked patient anatomy model(s) by positioning and orienting the retrieved mocked patient anatomy model(s) with respect to the patient-specific model and at a same point of view as the patient-specific model. For example, the anatomic orientation indicator processor 160 may identify a coordinate system of the patient-specific model. For example, an origin coordinate system of a heart valve may be defined as a center of the valve and the three axis may be the normal to the valve plane, a main anatomical axis (e.g., a four chamber (4CH) view direction for a tricuspid valve or an anteroposterior view for a mitral valve), and a cross product of the normal to the valve plane and the main anatomical axis. The anatomic orientation indicator processor 160 may be configured to compute and apply the position and orientation of the mocked patient anatomy model(s) to the coordinate system of the patient-specific model.

The anatomic orientation indicator processor 160 may comprise suitable logic, circuitry, interfaces and/or code that may be operable to present the anatomic orientation indicator with the patient-specific model at display system 134. For example, the anatomic orientation indicator processor 160 may be configured to identify the point of view of the patient-specific model. The point of view of the patient-specific model may be an initial default point of view, a point of view selected via user input device 130, or any suitable point of view. The anatomic orientation indicator processor 160 may comprise suitable logic, circuitry, interfaces and/or code that may be operable to update the position and orientation of the anatomic orientation indicator in response to a change in the point of view of the patient-specific model such that the point of view of the anatomic orientation indicator matches the point of view of the patient-specific model. For example, the signal processor 132 and/or anatomic orientation indicator processor 160 may receive an instruction from user input device 130 to change the point of view of the patient-specific model (e.g., a mouse input to rotate the patient-specific model). In response, the anatomic orientation indicator processor 160 may change the point of view of the anatomic orientation indicator (e.g., rotate the anatomic orientation indicator) to match the new point of view of the patient-specific model. In an exemplary embodiment, the anatomic orientation indicator processor 160 smoothly updates the point of view of the anatomic orientation indicator in substantially real-time such that the rotation of the points of view of the patient-specific model and the mocked patient anatomy model(s) of the anatomic orientation indicator is synchronized.

In various embodiments, the anatomic orientation indicator processor 160 may present the anatomic orientation indicator in one or more of a variety of selectable and/or default manners. For example, a full-size patient-specific model may be presented at display system 134 with a smaller anatomic orientation indicator comprising mocked patient anatomy models of the anatomy depicted in the patient-specific model and one or more anatomical structures nearby the anatomy depicted in the patient-specific model as illustrated, for example, in FIGS. 2-3 as described below. As another example, a full-size patient-specific model may be presented at display system 134 with a smaller anatomic orientation indicator comprising a smaller copy of the patient-specific model and mocked patient anatomy models of one or more anatomical structures nearby the anatomy depicted in the patient-specific model as illustrated, for example, in FIG. 4 as described below. As another example, a full-size anatomic orientation indicator may be presented at display system 134 comprising the patient-specific model and mocked patient anatomy models of one or more anatomical structures nearby the anatomy depicted in the patient-specific model as illustrated, for example, in FIG. 5 as described below.

Figure 2:
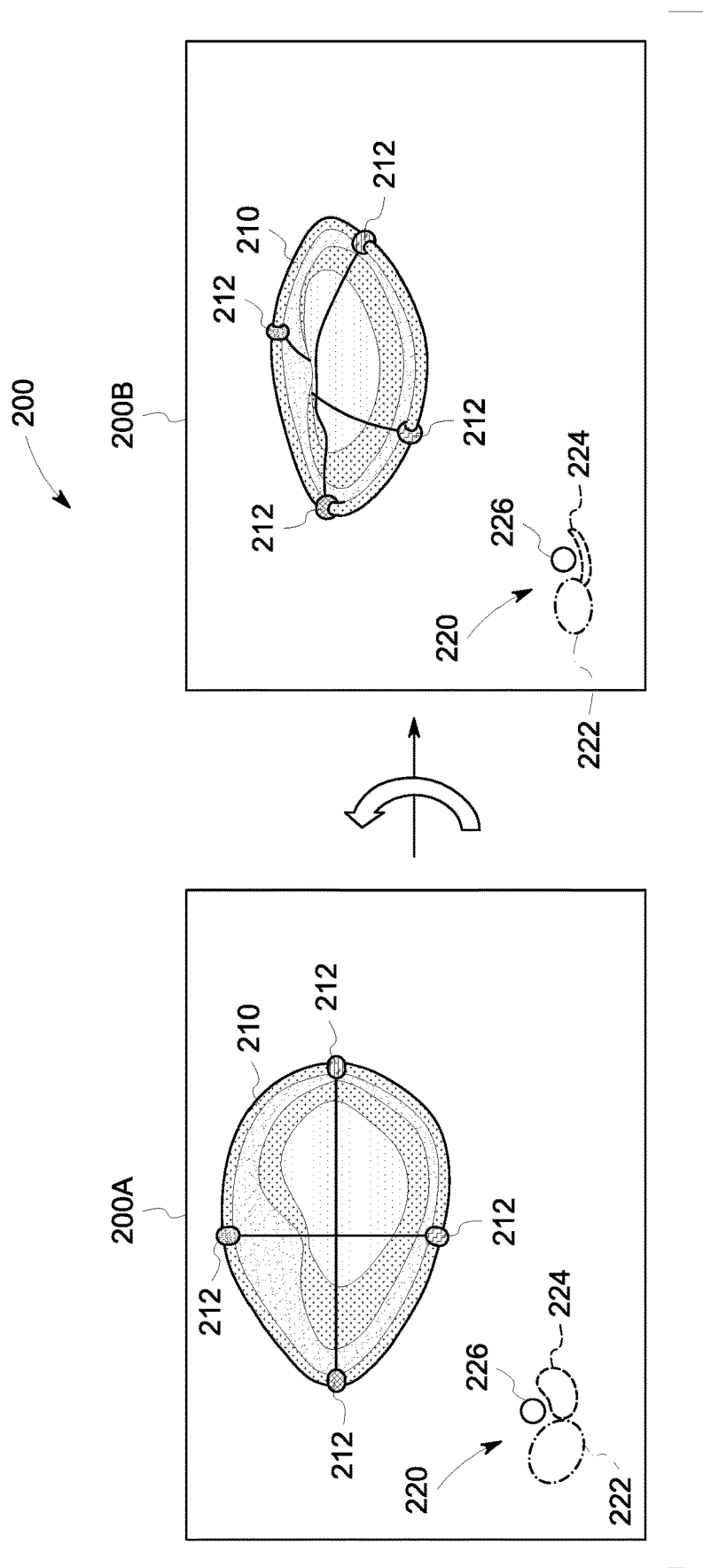
FIG. 2 illustrates exemplary displays of an anatomic orientation indicator with a patient-specific model of an anatomical structure of interest at a first point of view and a second point of view, in accordance with various embodiments.

FIG. 2 illustrates exemplary displays 200, 200A, 200B of an anatomic orientation indicator 220 with a patient-specific model 210 of an anatomical structure of interest at a first point of view 200A and a second point of view 200B, in accordance with various embodiments. Referring to FIG. 2, a first display 200A presents a patient-specific model 210 and anatomic orientation indictor 220 at a first point of view. The patient-specific model 210 comprises landmarks 212 that may have been selected and/or otherwise identified during extraction of the anatomical structure from a 3D volume. The patient-specific model 210 may be, for example, a model of a tricuspid valve of a patient or any suitable anatomical structure. The patient-specific model 210 may be generated from anatomical structure information extracted from a 3D volume acquired from a patient. The anatomic orientation indicator 220 may comprise mocked patient anatomy models of the anatomy depicted in the patient-specific model and nearby anatomical structures. For example, the anatomic orientation indicator 220 may comprise a mocked patient anatomy model of the tricuspid valve 222, a mocked patient anatomy model of the aortic valve 224, and a mocked patient anatomy model of the mitral valve 226. The mocked patient anatomy models 222, 224, 226 of the anatomic orientation indicator 220 may be presented at a first point of view corresponding with the first point of view of the patient-specific model 210. In various embodiments, the signal processor 132 may receive an instruction to change the point of view of the patient-specific model 210. For example, a user may use a mouse, touch screen, trackball, or any suitable user input device 130 to rotate the patient-specific model 210 to a second point of view 200B. In response to the user input changing the point of view from the first point of view 200A to the second point of view 200B, the patient-specific model 210 and anatomic orientation indicator 220 may be simultaneously and smoothly updated to the second point of view 200B. Accordingly, the anatomic orientation indicator 220 continuously provides spatial context information with respect to the patient-specific model 210. The patient-specific model 210 and anatomic orientation indicator 220 may be presented at a display 200, 200A, 200B of a display system 134 and/or may be stored at archive 138 or any suitable data storage medium.

Figure 3:
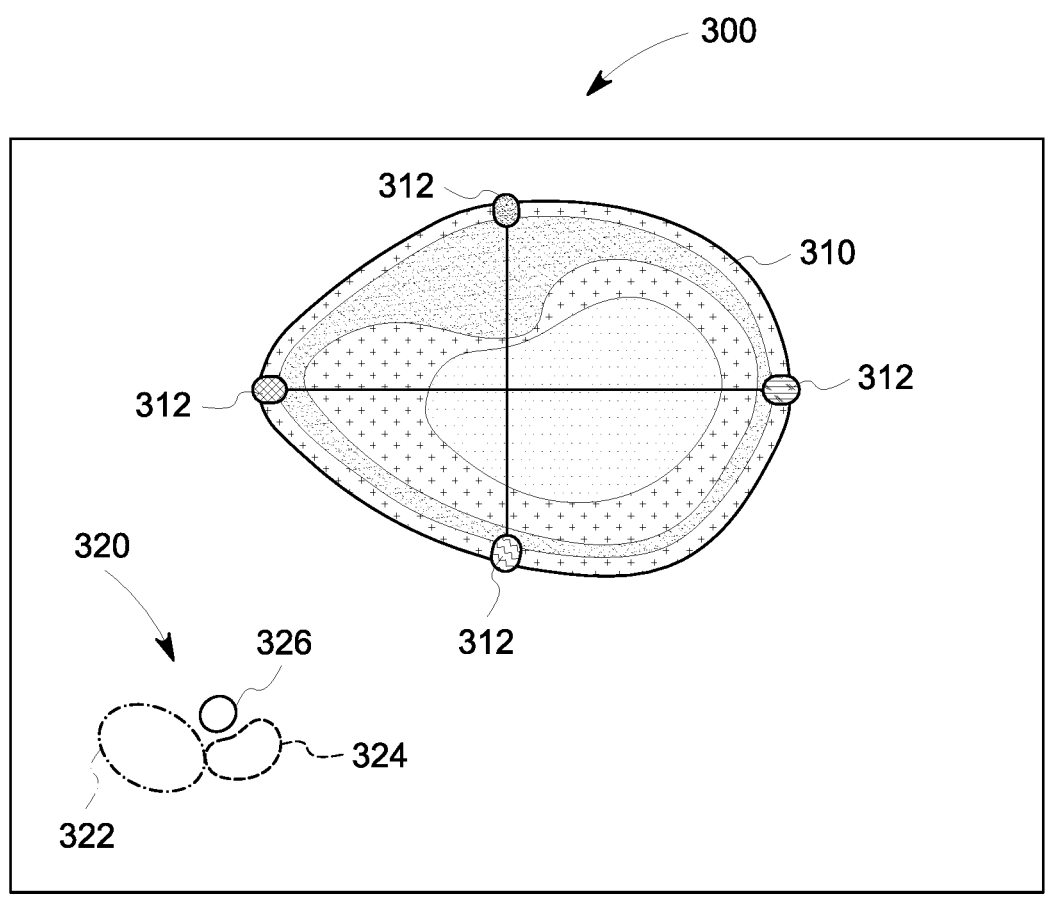
FIG. 3 is an exemplary display of an anatomic orientation indicator with a patient-specific model of an anatomical structure of interest, the anatomic orientation indicator comprising mocked patient anatomy models of the anatomical structure of interest and nearby anatomical structures, in accordance with various embodiments.

FIG. 3 is an exemplary display 300 of an anatomic orientation indicator 320 with a patient-specific model 310 of an anatomical structure of interest, the anatomic orientation indicator 320 comprising mocked patient anatomy models 322, 324, 326 of the anatomical structure of interest 322 and nearby anatomical structures 324, 326, in accordance with various embodiments. Referring to FIG. 3, the display 300 presents a patient-specific model 310 and anatomic orientation indictor 320. The patient-specific model 310 comprises landmarks 312 that may have been selected and/or otherwise identified during extraction of the anatomical structure from a 3D volume. The patient-specific model 310 may be, for example, a model of a tricuspid valve of a patient or any suitable anatomical structure. The patient-specific model 310 may be generated from anatomical structure information extracted from a 3D volume acquired from a patient. The anatomic orientation indicator 320 may comprise mocked patient anatomy models of the anatomy depicted in the patient-specific model and nearby anatomical structures. For example, the anatomic orientation indicator 320 may comprise a mocked patient anatomy model of the tricuspid valve 322, a mocked patient anatomy model of the aortic valve 324, and a mocked patient anatomy model of the mitral valve 326. The mocked patient anatomy models 322, 324, 326 of the anatomic orientation indicator 320 may be presented at a point of view corresponding with the point of view of the patient-specific model 310. The patient-specific model 310 and anatomic orientation indicator 320 may be presented at a display 300 of a display system 134 and/or may be stored at archive 138 or any suitable data storage medium.

Figure 4:
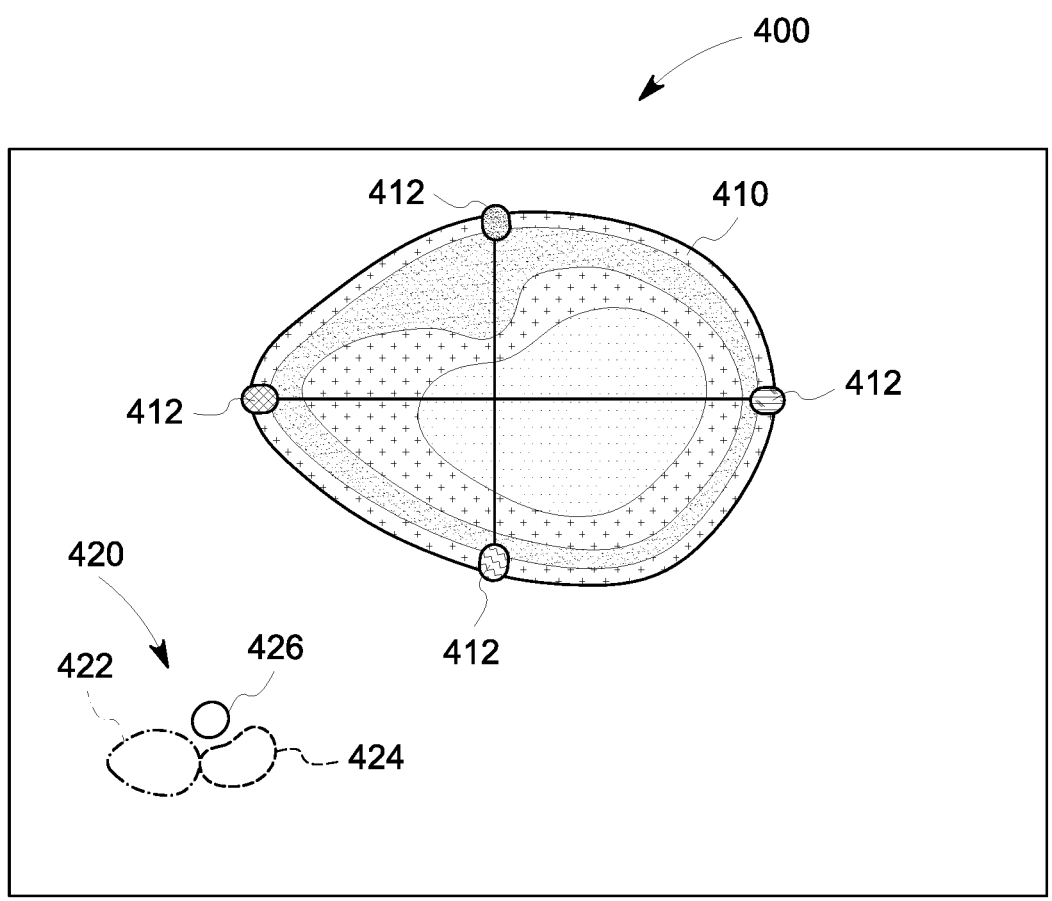
FIG. 4 is an exemplary display of an anatomic orientation indicator with a patient-specific model of an anatomical structure of interest, the anatomic orientation indicator comprising the patient-specific model and mocked patient anatomy models of nearby anatomical structures, in accordance with various embodiments.

FIG. 4 is an exemplary display 400 of an anatomic orientation indicator 420 with a patient-specific model 410 of an anatomical structure of interest, the anatomic orientation indicator 420 comprising the patient-specific model 422 and mocked patient anatomy models 424, 426 of nearby anatomical structures, in accordance with various embodiments. Referring to FIG. 4, the display 400 presents a patient-specific model 410 and anatomic orientation indictor 420. The patient-specific model 410 comprises landmarks 412 that may have been selected and/or otherwise identified during extraction of the anatomical structure from a 3D volume. The patient-specific model 410 may be, for example, a model of a tricuspid valve of a patient or any suitable anatomical structure. The patient-specific model 410 may be generated from anatomical structure information extracted from a 3D volume acquired from a patient. The anatomic orientation indicator 420 may comprise mocked patient anatomy models of the anatomy depicted in the patient-specific model and nearby anatomical structures. For example, the anatomic orientation indicator 420 may comprise a copy of the patient-specific model of the tricuspid valve 322, a mocked patient anatomy model of the aortic valve 424, and a mocked patient anatomy model of the mitral valve 426. The patient-specific model 422 and mocked patient anatomy models 424, 426 of the anatomic orientation indicator 420 may be presented at a point of view corresponding with the point of view of the patient-specific model 410. The patient-specific model 410 and anatomic orientation indicator 420 may be presented at a display 400 of a display system 134 and/or may be stored at archive 138 or any suitable data storage medium.

Figure 5:
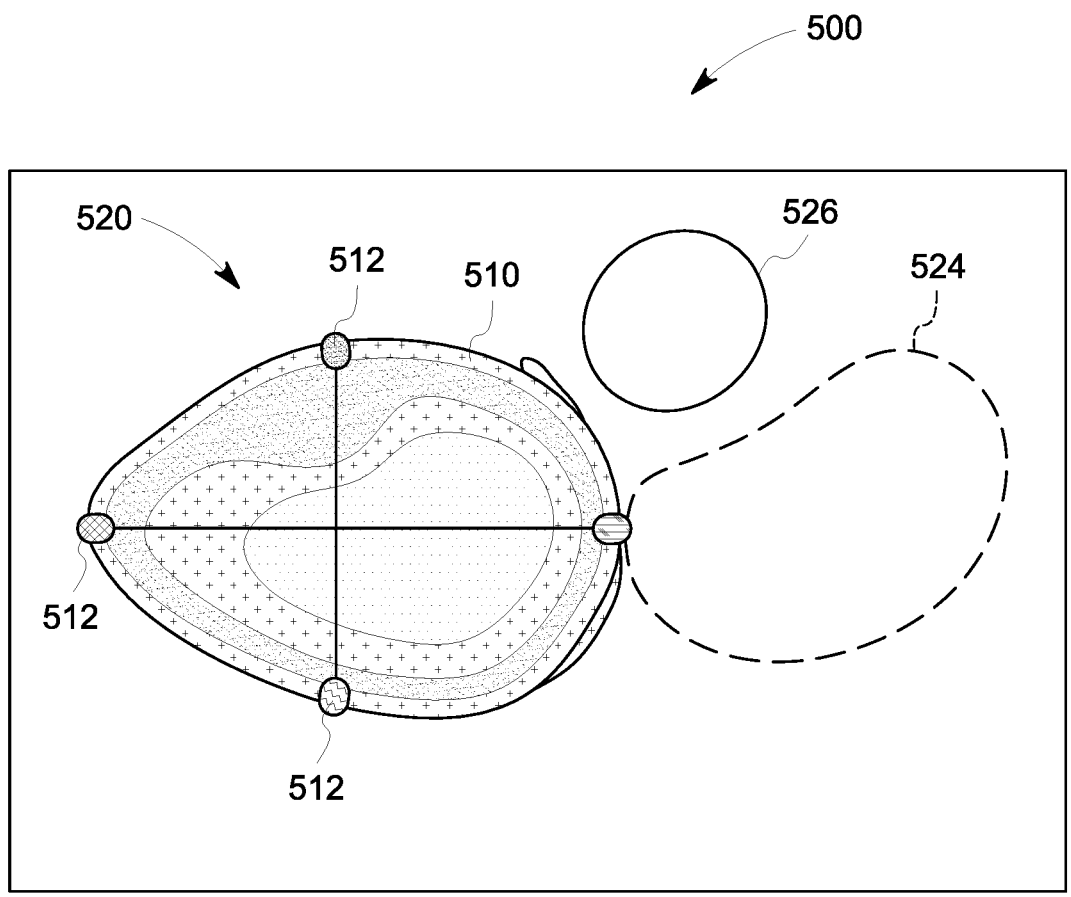
FIG. 5 is an exemplary display of an anatomic orientation indicator comprising a patient-specific model of an anatomical structure of interest and mocked patient anatomy models of nearby anatomical structures, in accordance with various embodiments.

FIG. 5 is an exemplary display 500 of an anatomic orientation indicator 520 comprising a patient-specific model 510 of an anatomical structure of interest and mocked patient anatomy models 524, 526 of nearby anatomical structures, in accordance with various embodiments. Referring to FIG. 5, the display 500 presents an anatomic orientation indictor 520 comprising a patient-specific model 510 and mocked patient anatomy models 524, 526 of nearby anatomical structures. The patient-specific model 510 comprises landmarks 412 that may have been selected and/or otherwise identified during extraction of the anatomical structure from a 3D volume. The patient-specific model 510 may be, for example, a model of a tricuspid valve of a patient or any suitable anatomical structure. The patient-specific model 510 may be generated from anatomical structure information extracted from a 3D volume acquired from a patient. The mocked patient anatomy models of nearby anatomical structures may comprise, for example, a mocked patient anatomy model of the aortic valve 524 and a mocked patient anatomy model of the mitral valve 526. The mocked patient anatomy models 524, 526 of the anatomic orientation indicator 520 may be presented at a point of view corresponding with the point of view of the patient-specific model 510 of the anatomic orientation indicator 520. The anatomic orientation indicator 520 may be presented at a display 500 of a display system 134 and/or may be stored at archive 138 or any suitable data storage medium.

Referring again to FIG. 1, the display system 134 may be any device capable of communicating visual information to a user. For example, a display system 134 may include a liquid crystal display, a light emitting diode display, and/or any suitable display or displays. The display system 134 can be operable to display information from the signal processor 132 and/or archive 138, such as patient-specific models 210, 310, 410, 422, 510, anatomic orientation indicators 220, 320, 420, 520, and/or any suitable information.

The archive 138 may be one or more computer-readable memories integrated with the ultrasound system 100 and/or communicatively coupled (e.g., over a network) to the ultrasound system 100, such as a Picture Archiving and Communication System (PACS), an enterprise archive (EA), a vendor-neutral archive (VNA), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things. In various embodiments, the archive 138 stores patient-specific models 210, 310, 410, 422, 510, anatomic orientation indicators 220, 320, 420, 520, mocked patient anatomy models 222, 224, 226, 322, 324, 326, 424, 426, 524, 526 associated with anatomical structures depicted in patient-specific models 210, 310, 410, 422, 510, instructions for extracting anatomical structures from 3D volumes, segmentation information generated by the anatomical structure extraction processor 140, instructions for defining mocked patient anatomy models, instructions for retrieving one or more mocked patient anatomy models, and/or instructions for generating and displaying an anatomic orientation indicator, among other things.

Figure 6:
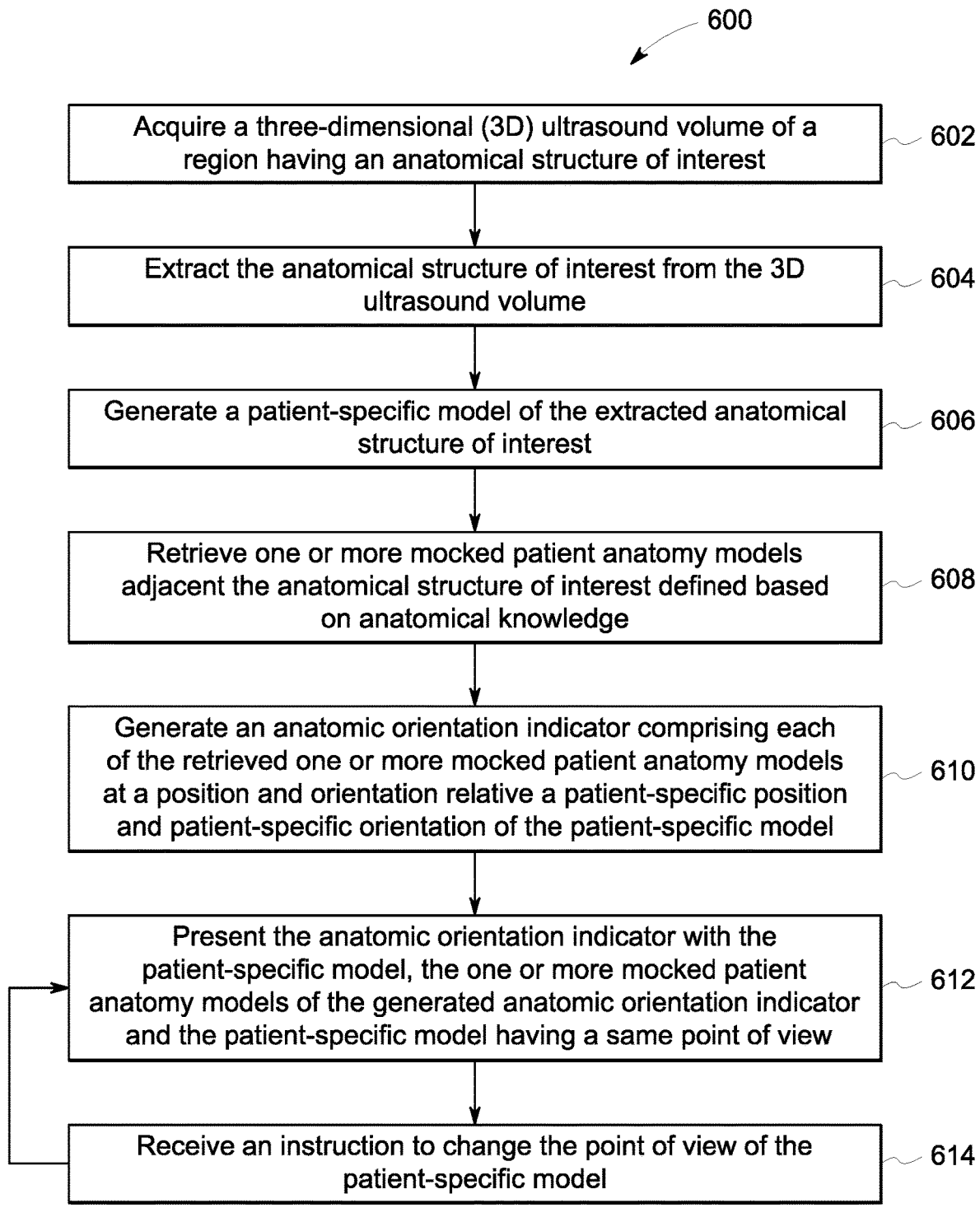
FIG. 6 is a flow chart illustrating exemplary steps that may be utilized for providing an anatomic orientation indicator with a patient-specific model of an anatomical structure of interest extracted from a three-dimensional (3D) ultrasound volume, in accordance with exemplary embodiments.

FIG. 6 is a flow chart 600 illustrating exemplary steps 602-614 that may be utilized for providing an anatomic orientation indicator 220, 320, 420, 520 with a patient-specific model 210, 310, 410, 422, 510 of an anatomical structure of interest extracted from a three-dimensional (3D) ultrasound volume, in accordance with exemplary embodiments. Referring to FIG. 6, there is shown a flow chart 600 comprising exemplary steps 602 through 614. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 602, an ultrasound system 100 may acquire a 3D ultrasound volume of a region having an anatomical structure of interest. For example, an ultrasound probe 104 of the ultrasound system 100 may acquire a 3D volume of a heart or any suitable anatomical structure.

At step 604, a signal processor 132 of the ultrasound system 100 may extract the anatomical structure of interest from the 3D volume. For example, an anatomical structure extraction processor 140 of the ultrasound system 100 may extract an anatomical structure of interest, such as a valve, ventricle, or vessel of a heart from the 3D volume acquired at step 602. The anatomical structure extraction processor 140 may extract the anatomical structure of interest from the 3D volume using image segmentation, manual tracing, and/or any suitable anatomical structure extraction technique.

At step 606, the signal processor 132 of the ultrasound system 100 may generate a patient-specific model 210, 310, 410, 422, 510 of the extracted anatomical structure of interest. For example, the patient-specific model generation processor 150 of the signal processor 132 may be configured to generate a patient-specific model 210, 310, 410, 422, 510 based on the anatomical structure of interest information extracted at step 604. For example, the patient-specific model generation processor 150 may be configured to perform polygonal modeling, point cloud modeling, curve modeling, digital sculpting, and/or any suitable 3D modeling technique and/or algorithm using the extracted anatomical structure of interest information to generate the patient-specific model 210, 310, 410, 422, 510.

At step 608, the signal processor 132 of the ultrasound system 100 may retrieve one or more mocked patient anatomy models 224, 226, 324, 326, 424, 426, 524, 526 adjacent the anatomical structure of interest defined based on anatomical knowledge. For example, an anatomic orientation indicator processor 160 of the signal processor 132 may be configured to select and retrieve the mocked patient anatomy models from archive 138 and/or any suitable data storage medium. The mocked patient anatomy model(s) 222, 224, 226, 322, 324, 326, 424, 426, 524, 526 may be defined using average shape, dimensions, and orientation reported in scientific literature. The mocked patient anatomy models 224, 226, 324, 326, 424, 426, 524, 526 may include mocked patient anatomy models of anatomical structures adjacent the anatomical structure of interest depicted in the patient-specific model 210, 310, 410, 422, 510. In an exemplary embodiment, the anatomic orientation indicator processor 160 may also retrieve a mocked patient anatomy model of the anatomical structure of interest 222, 322.

At step 610, the signal processor 132 of the ultrasound system 100 may generate an anatomic orientation indicator 220, 320, 420, 520 comprising each of the retrieved one or more mocked patient anatomy models 222, 224, 226, 322, 324, 326, 424, 426, 524, 526 at a position and orientation relative a patient-specific position and patient-specific orientation of the patient-specific model 210, 310, 410, 422, 510. For example, the anatomic orientation indicator processor 160 of the signal processor 132 may be configured to generate the anatomic orientation indicator comprising the mocked patient anatomy model(s) 222, 224, 226, 322, 324, 326, 424, 426, 524, 526 by positioning and orienting the retrieved mocked patient anatomy model(s) 222, 224, 226, 322, 324, 326, 424, 426, 524, 526 with respect to the patient-specific model 210, 310, 410, 422, 510 and at a same point of view as the patient-specific model 210, 310, 410,

422, 510. For example, the anatomic orientation indicator processor 160 may identify a coordinate system of the patient-specific model 210, 310, 410, 422, 510 and apply the position and orientation of the mocked patient anatomy model(s) 222, 224, 226, 322, 324, 326, 424, 426, 524, 526 to the coordinate system of the patient-specific model 210, 310, 410, 422, 510.

At step 612, the signal processor 132 of the ultrasound system 100 may present the anatomic orientation indicator 220, 320, 420, 520 with the patient-specific model 210, 310, 410, 422, 510, the one or more mocked patient anatomy models 222, 224, 226, 322, 324, 326, 424, 426, 524, 526 of the anatomic orientation indicator 220, 320, 420, 520 and the patient-specific model 210, 310, 410, 422, 510 having a same point of view. For example, the anatomic orientation indicator processor 160 of the signal processor 132 may be configured to present the anatomic orientation indicator 220, 320, 420, 520 with the patient-specific model 210, 310, 410, 422, 510 at display system 134. The anatomic orientation indicator processor 160 may be configured to identify the point of view of the patient-specific model 210, 310, 410, 422, 510. The point of view of the patient-specific model 210, 310, 410, 422, 510 may be an initial default point of view, a point of view selected via user input device 130, or any suitable point of view. The anatomic orientation indicator processor 160 may present the anatomic orientation indicator 220, 320, 420, 520 in one or more of a variety of selectable and/or default manners, for example, as described above with respect to FIGS. 2-5.

At step 614, the signal processor 132 of the ultrasound system 100 may receive an instruction to change the point of view of the patient-specific model 210, 310, 410, 422, 510. For example, the signal processor 132 and/or the anatomic orientation indicator processor 160 may receive an instruction from user input device 130 to change the point of view of the patient-specific model (e.g., a mouse, trackball, and/or touchscreen input to rotate the patient-specific model). In response, the process may return to step 612 and the anatomic orientation indicator processor 160 may change the point of view of the anatomic orientation indicator (e.g., rotate the anatomic orientation indicator) to match the new point of view of the patient-specific model 210, 310, 410, 422, 510. In a representative embodiment, the anatomic orientation indicator processor 160 smoothly updates the point of view of the anatomic orientation indicator 220, 320, 420, 520 in substantially real-time such that the rotation of the points of view of the patient-specific model 210, 310, 410, 422, 510 and the mocked patient anatomy model(s) 222, 224, 226, 322, 324, 326, 424, 426, 524, 526 of the anatomic orientation indicator 220, 320, 420, 520 is synchronized.

Aspects of the present disclosure provide an anatomic orientation indicator 220, 320, 420, 520 with a patient-specific model 210, 310, 410, 422, 510 of an anatomical structure of interest extracted from a three-dimensional (3D) ultrasound volume. In accordance with various embodiments, the method 600 may comprise extracting 604, by at least one processor 132, 140 of an ultrasound system 100, an anatomical structure of interest from a three-dimensional (3D) volume. The method 600 may comprise generating 606, by the at least one processor 132, 150, a patient-specific model 210, 310, 410, 422, 510 of the anatomical structure of interest extracted from the 3D volume. The method 600 may comprise generating 610, by the at least one processor 132, 160, an anatomic orientation indicator 220, 320, 420, 520 comprising at least one mocked patient anatomy model 224, 226, 324, 326, 424, 426, 524, 526 of an anatomical structure adjacent the anatomical structure of interest at a position and orientation relative a patient-specific position and patient-specific orientation of the patient-specific model 210, 310, 410, 422, 510. The method 600 may comprise displaying 612, by the at least one processor 132, 160 at a display system 134 of the ultrasound system 100, the anatomic orientation indicator 220, 320, 420, 520 with the patient-specific model 210, 310, 410, 422, 510. The at least one mocked patient anatomy model 224, 226, 324, 326, 424, 426, 524, 526 of the anatomic orientation indicator 220, 320, 420, 520 and the patient-specific model 210, 310, 410, 422, 510 may be displayed at a same first point of view 200A, 300, 400, 500. The method 600 may comprise receiving 614, by the at least one processor 132, 160, an instruction to change a point of view 200A, 300, 400, 500 of the patient-specific model 210, 310, 410, 422, 510 to a second point of view 200B. The method 600 may comprise updating, by the at least one processor 132, 160 at the display system 134, the displaying 612 of the anatomic orientation indicator 220, 320, 420, 520 with the patient-specific model 210, 310, 410, 422, 510 to the second point of view 200B.

In a representative embodiment, the method 600 may comprise acquiring 602, by an ultrasound probe 104 of the ultrasound system 100, the 3D volume of a region having the anatomical structure of interest. In an exemplary embodiment, the updating the displaying 612 of the anatomic orientation indicator 220, 320, 420, 520 with the patient-specific model 210, 310, 410, 422, 510 to the second point of view 200B may be a smooth, synchronized transition to the second point of view 200B. In various embodiments, the method 600 may comprise retrieving 608, by the at least one processor 132, 160, the at least one mocked patient anatomy model 224, 226, 324, 326, 424, 426, 524, 526 from a data storage medium 138. In certain embodiments, the at least one mocked patient anatomy model 224, 226, 324, 326, 424, 426, 524, 526 may be defined using an average reported shape, average reported dimensions, and average reported orientation of a plurality of the anatomical structure adjacent the anatomical structure of interest. In a representative embodiment, the anatomic orientation indicator 220, 320, 420, 520 may comprise the at least one mocked patient anatomy model 224, 226, 324, 326, 424, 426, 524, 526 and a mocked patient anatomy model 222, 322 of the anatomical structure of interest. In an exemplary embodiment, the anatomic orientation indicator 220, 320, 420, 520 may comprise the patient-specific model 422, 510 and the at least one mocked patient anatomy model 224, 226, 324, 326, 424, 426, 524, 526.

Various embodiments provide an ultrasound system 100 for providing an anatomic orientation indicator 220, 320, 420, 520 with a patient-specific model 210, 310, 410, 422, 510 of an anatomical structure of interest extracted from a three-dimensional (3D) ultrasound volume. The ultrasound system 100 may comprise at least one processor 132, 140, 150, 160 and a display system 134. The at least one processor 132, 140 may be configured to extract an anatomical structure of interest from a three-dimensional (3D) volume. The at least one processor 132, 150 may be configured to generate a patient-specific model 210, 310, 410, 422, 510 of the anatomical structure of interest extracted from the 3D volume. The at least one processor 132, 160 may be configured to generate an anatomic orientation indicator 220, 320, 420, 520 comprising at least one mocked patient anatomy model 224, 226, 324, 326, 424, 426, 524, 526 of an anatomical structure adjacent the anatomical structure of interest at a position and orientation relative a patient-specific position and patient-specific orientation of the patient-specific model 210, 310, 410, 422, 510. The at least one processor 132, 160 may be configured to display the anatomic orientation indicator 220, 320, 420, 520 with the patient-specific model 210, 310, 410, 422, 510 at a display system 134. The at least one mocked patient anatomy model 224, 226, 324, 326, 424, 426, 524, 526 of the anatomic orientation indicator 220, 320, 420, 520 and the patient-specific model 210, 310, 410, 422, 510 may be displayed at a same first point of view 200A, 300, 400, 500. The at least one processor 132, 160 may be configured to receive an instruction to change a point of view 200A, 300, 400, 500 of the patient-specific model 210, 310, 410, 422, 510 to a second point of view 200B. The at least one processor 132, 160 may be configured to update the display 200A, 300, 400, 500 of the anatomic orientation indicator with the patient-specific model 210, 310, 410, 422, 510 at the display system 134 to the second point of view 200B. The display system 134 may be configured to display the anatomic orientation indicator 220, 320, 420, 520 with the patient-specific model 210, 310, 410, 422, 510 at the same first point of view 200A, 300, 400, 500 and at the second point of view 200B.

In an exemplary embodiment, the ultrasound system 100 may comprise an ultrasound probe 104 operable to acquire the 3D volume of a region having the anatomical structure of interest. In various embodiments, the at least one processor 132, 160 may be configured to update the display 200A, 300, 400, 500 of the anatomic orientation indicator 220, 320, 420, 520 with the patient-specific model 210, 310, 410, 422, 510 to the second point of view 200B as a smooth, synchronized transition to the second point of view 200B. In certain embodiments, the ultrasound system 100 may comprise a data storage medium 138. The at least one processor 132, 160 may be configured to retrieve the at least one mocked patient anatomy model 224, 226, 324, 326, 424, 426, 524, 526 from the data storage medium 138. In a representative embodiment, the at least one mocked patient anatomy model 224, 226, 324, 326, 424, 426, 524, 526 may be defined using an average reported shape, average reported dimensions, and average reported orientation of a plurality of the anatomical structure adjacent the anatomical structure of interest. In an exemplary embodiment, the anatomic orientation indicator 220, 320, 420, 520 may comprise the at least one mocked patient anatomy model 224, 226, 324, 326, 424, 426, 524, 526 and a mocked patient anatomy model 222, 322 of the anatomical structure of interest. In various embodiments, the anatomic orientation indicator 220, 320, 420, 520 may comprise the patient-specific model 422, 510 and the at least one mocked patient anatomy model 224, 226, 324, 326, 424, 426, 524, 526.

Certain embodiments provide a non-transitory computer readable medium having stored thereon, a computer program having at least one code section. The at least one code section is executable by a machine for causing an ultrasound system to perform steps 600. The steps 600 may comprise extracting 604 an anatomical structure of interest from a three-dimensional (3D) volume. The steps 600 may comprise generating 606 a patient-specific model 210, 310, 410, 422, 510 of the anatomical structure of interest extracted from the 3D volume. The steps 600 may comprise generating 610 an anatomic orientation indicator 220, 320, 420, 520 comprising at least one mocked patient anatomy model 224, 226, 324, 326, 424, 426, 524, 526 of an anatomical structure adjacent the anatomical structure of interest at a position and orientation relative a patient-specific position and patient-specific orientation of the patient-specific model 210, 310, 410, 422, 510. The steps 600 may comprise displaying 612, at a display system 134 of the ultrasound system 100, the anatomic orientation indicator 220, 320, 420, 520 with the patient-specific model 210, 310, 410, 422, 510. The at least one mocked patient anatomy model 224, 226, 324, 326, 424, 426, 524, 526 of the anatomic orientation indicator 220, 320, 420, 520 and the patient-specific model 210, 310, 410, 422, 510 may be displayed at a same first point of view 200A, 300, 400, 500. The steps 600 may comprise receiving 614 an instruction to change a point of view 200A, 300, 400, 500 of the patient-specific model 210, 310, 410, 422, 510 to a second point of view 200B. The steps 600 may comprise updating the displaying 612 of the anatomic orientation indicator 220, 320, 420, 520 with the patient-specific model 210, 310, 410, 422, 510 to the second point of view 200B at the display system 134.

In various embodiments, the updating the displaying 612 of the anatomic orientation indicator 220, 320, 420, 520 with the patient-specific model 210, 310, 410, 422, 510 to the second point of view 200B may be a smooth, synchronized transition to the second point of view 200B. In certain embodiments, the steps 600 may comprise retrieving 608 the at least one mocked patient anatomy model 224, 226, 324, 326, 424, 426, 524, 526 from a data storage medium 138. In a representative embodiment, the at least one mocked patient anatomy model 224, 226, 324, 326, 424, 426, 524, 526 may be defined using an average reported shape, average reported dimensions, and average reported orientation of a plurality of the anatomical structure adjacent the anatomical structure of interest. In an exemplary embodiment, the anatomic orientation indicator 220, 320, 420, 520 may comprise the at least one mocked patient anatomy model 224, 226, 324, 326, 424, 426, 524, 526 and a mocked patient anatomy model 222, 322 of the anatomical structure of interest. In various embodiments, the anatomic orientation indicator 220, 320, 420, 520 may comprise the patient-specific model 422, 510 and the at least one mocked patient anatomy model 224, 226, 324, 326, 424, 426, 524, 526.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" or "configured" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for providing an anatomic orientation indicator with a patient-specific model of an anatomical structure of interest extracted from a three-dimensional (3D) ultrasound volume.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method comprising:
   extracting, by at least one processor of an ultrasound system, an anatomical structure of interest internal to a patient from a three-dimensional (3D) volume;
   generating, by the at least one processor, a patient-specific model of the anatomical structure of interest extracted from the 3D volume;
   generating, by the at least one processor, an anatomic orientation indicator comprising at least one mocked patient anatomy model of an anatomical structure adjacent the anatomical structure of interest at a position and orientation relative a patient-specific position and patient-specific orientation of the patient-specific model, wherein the anatomical structure adjacent the anatomical structure of interest is internal to the patient, and wherein the at least one mocked patient anatomy model does not include the anatomical structure of interest;
   displaying, by the at least one processor at a display system of the ultrasound system, the anatomic orientation indicator with the patient-specific model, wherein the at least one mocked patient anatomy model of the anatomic orientation indicator and the patient-specific model are displayed at a same first point of view;
   receiving, by the at least one processor, an instruction to change a point of view of the patient-specific model to a second point of view; and
   updating, by the at least one processor at the display system, the displaying of the anatomic orientation indicator with the patient-specific model to the second point of view.

2. The method of claim 1, comprising acquiring, by an ultrasound probe of the ultrasound system, the 3D volume of a region having the anatomical structure of interest.

3. The method of claim 1, wherein the updating the displaying of the anatomic orientation indicator with the patient-specific model to the second point of view is a visually smooth, synchronized transition to the second point of view.

4. The method of claim 1, comprising retrieving, by the at least one processor, the at least one mocked patient anatomy model from a data storage medium.

5. The method of claim 1, wherein the at least one mocked patient anatomy model is defined using an average reported shape, average reported dimensions, and average reported orientation of a plurality of the anatomical structure adjacent the anatomical structure of interest.

6. The method of claim 1, wherein the anatomic orientation indicator comprises the at least one mocked patient anatomy model and a mocked patient anatomy model of the anatomical structure of interest.

7. The method of claim 1, wherein the anatomic orientation indicator comprises the patient-specific model and the at least one mocked patient anatomy model.

8. An ultrasound system comprising:
   at least one processor configured to:
      extract an anatomical structure of interest internal to a patient from a three-dimensional (3D) volume;
      generate a patient-specific model of the anatomical structure of interest extracted from the 3D volume;
      generate an anatomic orientation indicator comprising at least one mocked patient anatomy model of an anatomical structure adjacent the anatomical structure of interest at a position and orientation relative a patient-specific position and patient-specific orientation of the patient-specific model, wherein the anatomical structure adjacent the anatomical structure of interest is internal to the patient, and wherein the at least one mocked patient anatomy model does not include the anatomical structure of interest;
      display the anatomic orientation indicator with the patient-specific model at a display system, wherein the at least one mocked patient anatomy model of the anatomic orientation indicator and the patient-specific model are displayed at a same first point of view;
      receive an instruction to change a point of view of the patient-specific model to a second point of view; and
      update the display of the anatomic orientation indicator with the patient-specific model at the display system to the second point of view; and
   the display system configured to display the anatomic orientation indicator with the patient-specific model at the same first point of view and at the second point of view.

9. The system of claim 8, comprising an ultrasound probe operable to acquire the 3D volume of a region having the anatomical structure of interest.

10. The system of claim 8, wherein the at least one processor is configured to update the display of the anatomic orientation indicator with the patient-specific model to the second point of view as a visually smooth, synchronized transition to the second point of view.

11. The system of claim 8, comprising a data storage medium, wherein the at least one processor is configured to retrieve the at least one mocked patient anatomy model from the data storage medium.

12. The system of claim 8, wherein the at least one mocked patient anatomy model is defined using an average reported shape, average reported dimensions, and average reported orientation of a plurality of the anatomical structure adjacent the anatomical structure of interest.

13. The system of claim 8, wherein the anatomic orientation indicator comprises the at least one mocked patient anatomy model and a mocked patient anatomy model of the anatomical structure of interest.

14. The system of claim 8, wherein the anatomic orientation indicator comprises the patient-specific model and the at least one mocked patient anatomy model.

15. A non-transitory computer readable medium having stored thereon, a computer program having at least one code section, the at least one code section being executable by a machine for causing an ultrasound system to perform steps comprising:

extracting an anatomical structure of interest internal to a patient from a three-dimensional (3D) volume;

generating a patient-specific model of the anatomical structure of interest extracted from the 3D volume;

generating an anatomic orientation indicator comprising at least one mocked patient anatomy model of an anatomical structure adjacent the anatomical structure of interest at a position and orientation relative a patient-specific position and patient-specific orientation of the patient-specific model, wherein the anatomical structure adjacent the anatomical structure of interest is internal to the patient, and wherein the at least one mocked patient anatomy model does not include the anatomical structure of interest;

displaying, at a display system of the ultrasound system, the anatomic orientation indicator with the patient-specific model, wherein the at least one mocked patient anatomy model of the anatomic orientation indicator and the patient-specific model are displayed at a same first point of view;

receiving an instruction to change a point of view of the patient-specific model to a second point of view; and updating the displaying of the anatomic orientation indicator with the patient-specific model to the second point of view at the display system.

16. The non-transitory computer readable medium of claim 15, wherein the updating the displaying of the anatomic orientation indicator with the patient-specific model to the second point of view is a visually smooth, synchronized transition to the second point of view.

17. The non-transitory computer readable medium of claim 15, comprising retrieving the at least one mocked patient anatomy model from a data storage medium.

18. The non-transitory computer readable medium of claim 15, wherein the at least one mocked patient anatomy model is defined using an average reported shape, average reported dimensions, and average reported orientation of a plurality of the anatomical structure adjacent the anatomical structure of interest.

19. The non-transitory computer readable medium of claim 15, wherein the anatomic orientation indicator comprises the at least one mocked patient anatomy model and a mocked patient anatomy model of the anatomical structure of interest.

20. The non-transitory computer readable medium of claim 15, wherein the anatomic orientation indicator comprises the patient-specific model and the at least one mocked patient anatomy model.

* * * * *